(12) United States Patent
Wegner et al.

(10) Patent No.: US 6,423,873 B1
(45) Date of Patent: Jul. 23, 2002

(54) PROCESS FOR PREPARING PHOSPHONIUM SALTS

(75) Inventors: Christoph Wegner, Kirchheim; Michael John, Lambsheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/791,574

(22) Filed: Feb. 26, 2001

(30) Foreign Application Priority Data

Mar. 2, 2000 (DE) .......................................... 100 09 459

(51) Int. Cl.⁷ ................................................. C07F 9/54
(52) U.S. Cl. ........................................................... 568/9
(58) Field of Search ................................ 568/9; 585/600

(56) References Cited

U.S. PATENT DOCUMENTS

| 4,182,731 A | 1/1980 | Schulz et al. | |
| 5,166,445 A | 11/1992 | Meyer | |
| 5,208,381 A | 5/1993 | Meyer | |
| 6,187,959 B1 * | 2/2001 | Wegner et al. | 568/9 |

FOREIGN PATENT DOCUMENTS

| DE | 27 29 974 | 1/1979 |
| EP | 382 067 | 8/1990 |
| EP | 895 997 | 2/1999 |

OTHER PUBLICATIONS

J.Chem.Soc., 1965, 2019–26, Carotenoids and Related Compounds. Part XI. Manchand et al.

\* cited by examiner

*Primary Examiner*—Jean F. Vollano
(74) *Attorney, Agent, or Firm*—Keil & Weinkauf

(57) ABSTRACT

A process for preparing phosphonium salts of the general formula I

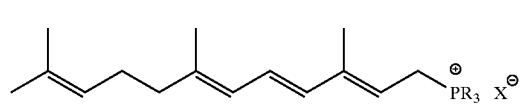

in which the substituents have the following meanings, independently of one another:

R aryl;

X anion of an organic or inorganic acid selected from the group consisting of hydrohalic acids, sulfuric acid, sulfonic acids, phosphoric acid and $C_1$–$C_6$-alkanoic acids, by reacting 3,7,11-trimethyldodeca-1,4,6,10-tetraen-3-ol of the formula II

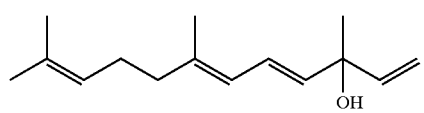

with triarylphosphane and organic or inorganic acids selected from the abovementioned group, wherein in a two-stage process a) initially a tertiary phosphonium salt of the formula III

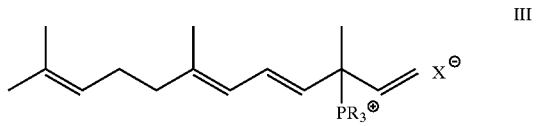

in which the radicals R and X have the abovementioned meanings, is prepared at temperatures in the range from −20 to 40° C., and b) the tertiary phosphonium salt of the formula III which is formed is rearranged to the primary phosphonium salt of the formula I at temperatures in the range from 40 to 100° C.

6 Claims, No Drawings

PROCESS FOR PREPARING PHOSPHONIUM SALTS

The present invention relates to a process for preparing 3,7,11-trimethyldodeca-2,4,6,10-tetraen-1-ylphosphonium salts.

The $C_{15}$ phosphonium salts for synthesizing carotenoids are usually prepared from vinyl carbinols by reaction with triphenylphosphane and a strong acid such as HCl or $H_2SO_4$ in protic solvents (see, for example, J. Chem. Soc., 1965, 2019–2026). Unlike vinyl-β-ionol, a precursor employed for synthesizing vitamin A and β-carotene, it is possible to convert vinylpseudoionol as precursor for preparing lycopene under these standard conditions into the corresponding $C_{15}$ phosphonium salts only with poor yields and with low E/Z selectivites.

EP-A-0 382 067 describes a process in which $C_{15}$ phosphonium salts of lower alkanoic acids are prepared as intermediates, because said salts of strong acids always provide poor E/Z selectivities at low yields in the following preparation of lycopene (byproducts). The salts of the alkanoic acids must be converted back into the chlorides by anion exchange in an elaborate procedure before the final Wittig olefination. To achieve a high E/Z ratio in the lycopene it is additionally necessary to remove contents of the (Z)-phosphonium salt by crystallization.

DE-A-27 29 974 discloses a process for preparing aqueous solutions of polyenyltriarylphosphonium salts of strong acids in acetic acid (see Example 3), although no 3,7,11-trimethyldodeca-2,4,6,10-tetraen-1-ylphosphonium salts are mentioned in the examples.

EP-A-0 895 997 describes a process for preparing $C_{15}$ phosphonium salts by reacting 3,7,11-trimethyldodeca-1,4,6,10-tetraen-3-ol with triarylphosphine and sulfonic acids in a solvent. The E/Z selectivities of the $C_{15}$ phosphonium salts achieved with this process are, however, still unsatisfactory.

It is an object of the present invention to provide a process for preparing $C_{15}$ phosphonium salts in which 3,7,11-trimethyldodeca-2,4,6,10-tetraen-1-ylphosphonium salts which have a high E content and which afford, for example in further reaction to lycopene, high E/Z selectivities are obtained.

We have found that this object is achieved by a process for preparing phosphonium salts of the general formula I

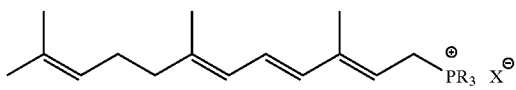

in which the substituents have the following meanings, independently of one another:

R aryl;

X anion of an organic or inorganic acid selected from the group consisting of hydrohalic acids, sulfuric acid, sulfonic acids, phosphoric acid and $C_1$–$C_6$-alkanoic acids, by reacting 3,7,11-trimethyldodeca-1,4,6,10-tetraen-3-ol of the formula II

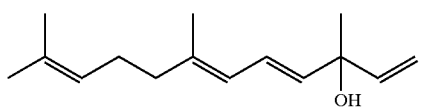

with triarylphosphine and organic or inorganic acids selected from the group consisting of hydrohalic acids, sulfuric acid, sulfonic acids, phosphoric acid and $C_1$–$C_6$-alkanoic acids, wherein in a two-stage process a) initially a tertiary phosphonium salt of the formula III

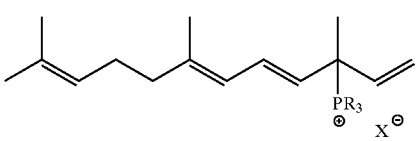

in which the radicals R and X have the abovementioned meanings, is prepared at temperatures in the range from −20 to 40° C., preferably in the range from −10 to 20° C., particularly preferably in the range from 0 to 15° C., and b) the tertiary phosphonium salt of the formula III which is formed is rearranged to the primary phosphonium salt of the formula I at temperatures in the range from 40 to 100° C., preferably in the range from 40 to 70° C., particularly preferably in the range from 42 to 60° C.

The alcohol of the formula II (3,7,11-trimethyldodeca-1,4,6,10-tetraen-3-ol) is also called vinyl-Ψ-ionol or vinylpseudoionol and is disclosed, for example, in J. Chem. Soc. 1965, 2023 or in EP 382 067. It can be obtained from pseudoionone by known methods.

The meaning of aryl for R in formulae I and III includes the usual aryl radicals occurring in phosphines and phosphonium salts, such as phenyl, tolyl, naphthyl, optionally substituted, preferably phenyl.

The hydrohalic acids for X mean, in particular, hydrochloric acid and hydrobromic acid.

The term sulfonic acids means aryl- and alkylsulfonic acids selected from the group consisting of $C_nH_{2n+1}$—$SO_3H$ with n=1 to 4, Ar—$SO_3H$ with Ar=phenyl, tolyl and $CF_3$—$SO_3H$. Preferred sulfonic acids are methanesulfonic acid, ethanesulfonic acid and p-toluenesulfonic acid.

The term $C_1$–$C_6$-alkanoic acids means straight-chain or branched carboxylic acids with 1 to 6 carbon atoms, such as, for example, formic acid, acetic acid, propionic acid, butyric acid, isobutyric acid, valeric acid and isovaleric acid. Preferred carboxylic acids are formic acid, acetic acid and propionic acid.

A particular embodiment of the process of the invention comprises carrying out the reaction in process step a) with sulfonic acids, preferably with sulfonic acids selected from the group consisting of $C_nH_{2n+1}$—$SO_3H$ with n=1 to 4, Ar—$SO_3H$ with Ar=phenyl, tolyl or $CF_3$—$SO_3H$, particularly preferably with methanesulfonic acid or ethanesulfonic acid, in the presence of $C_1$–$C_6$-alkanoic acids, preferably acetic acid or propionic acid, particularly preferably in the presence of acetic acid, as solvent.

This usually entails introducing the sulfonic acid into the solvent and adding the alcohols.

In order to achieve high E/Z selectivities in this procedure it is particularly advantageous to use acetic acid as solvent equimolar amounts of the abovementioned sulfonic acids.

It is also possible where appropriate to add an inert organic solvent to the reaction mixture. Preferred inert organic solvents are, inter alia, chlorinated or aromatic hydrocarbons, ethers, alcohols and esters, for example hexane, methylene chloride, chloroform, benzene, toluene, xylene, diisopropyl ether, tert-butyl methyl ether, tetrahydrofuran, methanol, ethanol and ethyl acetate.

The initial step a)—synthesis of the tert-phosphonium salt—takes place, depending on the reaction temperature, within from 2 to 120 minutes, preferably within from 10 to 90 minutes, particularly preferably within from 15 to 60 minutes.

The arrangement of the tertiary to the primary phosphonium salt in step b) takes place, depending on the temperature, within from 5 to 35 hours, preferably 10 to 30 hours, particularly preferably 15 to 25 hours.

It is possible with the process of the invention to convert vinylpseudoionol of the formula II with, for example, methanesulfonic acid in glacial acetic acid into the corresponding phosphonium salt in yields of 95% and with an E/Z selectivity of greater than 4:1. In this connection, Z means the total of all the Z isomers occurring: (2Z,6E)+(2E,6Z)+(2Z, 6Z).

The salt obtained in this way is suitable immediately for the Wittig reaction with 2,7-dimethyl-2,4,6-octatrienedial to prepare lycopene, it being possible to dispense with additional steps such as metathesis or enrichment of the E component by an additional crystallization.

The advantage of the novel variant of the invention for preparation via the tertiary 3-phosphonium salt is, inter alia, that significantly higher E/Z ratios are obtained. Whereas with a reaction in the temperature range from 60 to 80° C. —as disclosed in EP-A-0 895 997—in the system acetic acid/methanesulfonic acid/triphenylphosphine and E/Z selectivity of from 3.6 to 3.7:1 is achieved, the E/Z selectivities achieved by the novel method are greater than 4:1, preferably 4 to 5:1, particularly preferably 4.1 to 4.4:1.

Another advantage of the process of the invention is that the yields are distinctly higher and are 5 to 10% higher than in the comparable one-stage process variants which have been carried out at a higher temperature. This is also associated with distinctly less formation of byproducts (in particular the formation of hydroxy and acetoxy adducts).

These adducts react just like the required product (3,7,11-trimethyldodeca-2,4,6,10-tetraen-1-ylphosphonium salt of the formula I) in the Wittig reaction which has already been mentioned from the outset to give the corresponding lycopene analogs which can be removed from the lycopene final product only with difficulty.

The following examples are intended to illustrate the process of the invention in detail.

EXAMPLE 1

A mixture of triphenylphosphine (58 g, 217 mmol), acetic acid (280 g) and methanesulfonic acid (16.3 g, 170 mmol) was A introduced at 10° C. into a 1 L reactor. While stirring, vinylpseudoionol (37.4 g, 170 mmol) was added dropwise over the course of one hour. After stirring at 10° C. for 30 min, the reaction mixture was analyzed by HPLC. Vinylpseudoionol had been converted into 95% 3-phosphonium salt and 5% 1-phosphonium salt. The reaction mixture was then heated at 45° C. for 20 h. According to HPLC, the 3-phosphonium salt had completely rearranged into the 1-phosphonium salt. The E/Z ratio in the acetic acid solution was 4.2:1. HPLC analysis revealed a yield of 95%.

EXAMPLE 2

A mixture of triphenylphosphine (58 g, 217 mmol), acetic acid (280 g) and p-toluenesulfonic acid hydrate (32.3 g, 170 mmol) was introduced at 10° C. into a 1 L reactor. While stirring, vinylpseudoionol (37.4 g, 170 mmol) was added dropwise over the course of one hour. After stirring for 30 min, the mixture was heated at 45° C. for 20 h.

HPLC analysis revealed the following results: E/Z ratio in the acetic acid solution: 4.3:1; yield: 95%.

EXAMPLE 3

A mixture of triphenylphosphine (58 g, 217 mmol), acetic acid (280 g) and 85% phosphoric acid (19.6 g, 170 mmol) was introduced at 10° C. into a 1 L reactor. While stirring, vinylpseudoionol (37.4 g, 170 mmol) was added dropwise over the course of one hour. After stirring for 30 min, the mixture was heated at 45° C. for 20 h.

HPLC analysis revealed the following results: E/Z ratio in the acetic acid solution: 4.2:1; yield: 95%.

EXAMPLE 4

A mixture of triphenylphosphine (58 g, 217 mmol), acetic acid (280 g) and sulfuric acid (16.7 g, 170 mmol) was introduced at 10° C. into a 1 L reactor. While stirring, vinylpseudoionol (37.4 g, 170 mmol) was added dropwise over the course of one hour. After stirring for 30 min, the mixture was heated at 45° C. for 20 h.

HPLC analysis revealed the following results: E/Z ratio in the acetic acid solution: 4.1:1; yield: 95%.

EXAMPLE 5

A mixture of triphenylphosphine (58 g, 217 mmol), acetic acid (280 g) and methanesulfonic acid (16.3 g, 170 mmol) was introduced at 70° C. into a 1 L reactor. While stirring, vinylpseudoionol (37.4 g, 170 mmol) was added dropwise over the course of 10 min. After stirring at 70° C. for a further 30 min, the reaction mixture was analyzed by HPLC. The E/Z ratio in the acetic acid solution was 3.7:1. Quantitative HPLC revealed a yield of 91%.

We claim:

1. A process for preparing phosphonium salts of the general formula I

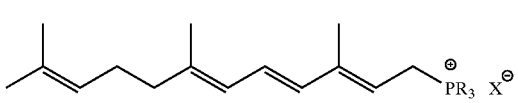

in which the substituents have the following meanings independently of one another:

R aryl;

X anion of an organic or inorganic acid selected from the group consisting of hydrohalic acids, sulfuric acid, sulfonic acids, phosphoric acid and $C_1$–$C_6$-alkanoic acids, by reacting 3,7,11-trimethyldodeca-1,4,6,10-tetraen-3-ol of the formula II

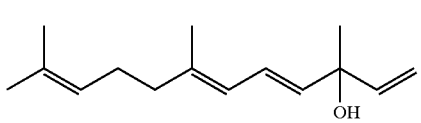

with triarylphosphine and organic or inorganic acids selected from the group consisting of hydrohalic acids, sulfuric acid, sulfonic acids, phosphoric acid and $C_1$–$C_6$-alkanoic acids, wherein in a two-stage process a) initially a tertiary phosphonium salt of the formula III

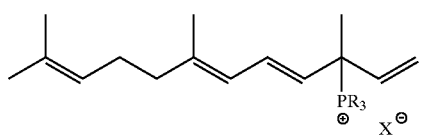

in which the radicals R and X have the above mentioned meanings, is prepared at temperatures in the range from 0 to 15° C., and b) the tertiary phosphonium salt of the formula III which is formed is rearranged to the primary phosphonium salt of the formula I at temperatures in the range from 40 to 100° C.

2. A process as claimed in claim 1, wherein the rearrangement of the tertiary phosphonium salt of the formula III in process stage b) is carried out at temperatures in the range from 40 to 60° C.

3. A process as claimed in claim 1, wherein the reaction in processstage a) is carried out with sulfonic acids in the presence of $C_1$–$C_6$-alkanoic acids.

4. A process as claimed in claim 3, wherein the reaction is carried out with sulfonic acids selected from the group consisting of $C_nH_{2n+1}$—$SO_3H$ with n=1 to 4, Ar—$SO_3H$ with Ar=phenyl, tolyl or $CF_3$—$SO_3H$ in the presence of acetic acid or propionic acid.

5. A process as claimed in claim 3, wherein the reaction is carried out with methanesulfonic acid or ethanesulfonic acid in the presence of acetic acid.

6. A process as claimed in claim 1 for preparing phosphonium salts of the general formula I with an E/Z selectivity of greater than 4:1.

* * * * *